United States Patent
Hjerten

(10) Patent No.: US 9,260,536 B2
(45) Date of Patent: Feb. 16, 2016

(54) CAPTURE OF PATHOGENIC AND NON-PATHOGENIC BIOPOLYMERS AND BIOPARTICLES

(76) Inventor: Stellan Hjerten, Uppsala (SE)

( * ) Notice: Subject to any disclaimer, the term of this patent is extended or adjusted under 35 U.S.C. 154(b) by 7 days.

(21) Appl. No.: 14/233,491

(22) PCT Filed: Jul. 20, 2012

(86) PCT No.: PCT/SE2012/050845
§ 371 (c)(1),
(2), (4) Date: Jan. 17, 2014

(87) PCT Pub. No.: WO2013/015738
PCT Pub. Date: Jan. 31, 2013

(65) Prior Publication Data
US 2014/0178439 A1    Jun. 26, 2014

(30) Foreign Application Priority Data

Jul. 22, 2011  (SE) ...................... 1150717

(51) Int. Cl.
| | |
|---|---|
| A61K 45/06 | (2006.01) |
| A61K 31/765 | (2006.01) |
| C08B 37/12 | (2006.01) |
| G01N 33/569 | (2006.01) |
| G01N 33/68 | (2006.01) |
| A61K 31/729 | (2006.01) |
| B01J 20/32 | (2006.01) |
| B01J 20/287 | (2006.01) |
| B01D 15/32 | (2006.01) |
| G01N 30/88 | (2006.01) |

(52) U.S. Cl.
CPC ............... *C08B 37/12* (2013.01); *A61K 31/729* (2013.01); *A61K 31/765* (2013.01); *A61K 45/06* (2013.01); *B01D 15/327* (2013.01); *B01J 20/287* (2013.01); *B01J 20/321* (2013.01); *B01J 20/3212* (2013.01); *B01J 20/3255* (2013.01); *B01J 20/3274* (2013.01); *G01N 33/569* (2013.01); *G01N 33/56911* (2013.01); *G01N 33/6803* (2013.01); *G01N 2030/8813* (2013.01)

(58) Field of Classification Search
None
See application file for complete search history.

(56) References Cited

U.S. PATENT DOCUMENTS

| | | | |
|---|---|---|---|
| 5,372,719 | A | 12/1994 | Afeyan et al. |
| 5,814,223 | A | 9/1998 | Hjerten et al. |
| 2006/0163149 | A1 | 7/2006 | Wadstrom et al. |
| 2008/0220413 | A1 | 9/2008 | Goldsborough |
| 2009/0214585 | A1 | 8/2009 | Ciocca et al. |

FOREIGN PATENT DOCUMENTS

| | | | |
|---|---|---|---|
| EP | 0 021 230 A2 | 1/1981 | |
| EP | 0 318 452 A1 | 5/1989 | |
| WO | 2004/110193 A1 | 12/2004 | |
| WO | 2006/110277 A1 | 10/2006 | |
| WO | 2009/017456 A1 | 2/2009 | |
| WO | WO 2009/017456 * | 2/2009 | ............. A61K 31/74 |
| WO | 2009/131526 A1 | 10/2009 | |

OTHER PUBLICATIONS

Hjerten, Chromatographiv Reviews, 1967, 9(2), 122.*
Hjerten et al., Journal of Chromatography, 1986, 359, 99.*
International Search Report, dated Oct. 24, 2012, from corresponding PCT application.
Extended European Search Report, dated Mar. 27, 2015, from corresponding EP application 12818100.5.

* cited by examiner

*Primary Examiner* — Karlheinz R Skowronek
*Assistant Examiner* — Roy Teller
(74) *Attorney, Agent, or Firm* — Young & Thompson

(57) ABSTRACT

A method of preparing a capturing agent for a selected biopolymer or bioparticle, includes the steps of:

a) selecting a desired biopolymer or bioparticle, and b) providing a support matrix modified to have, at predetermined conditions, such a net negative surface charge and net surface hydrophobicity in relation to the net negative surface charge and the net surface hydrophobicity of the selected biopolymer or bioparticle that the modified support matrix is capable of selective interaction and capture of the biopolymer or bioparticle through a resulting net hydrophobic interaction being the actual hydrophobic interaction minus the actual electrostatic repulsion. The use of such a capturing agent as a therapeutically active substance, as well as in chromatography and diagnosis are also disclosed.

28 Claims, No Drawings

_US 9,260,536 B2_

CAPTURE OF PATHOGENIC AND NON-PATHOGENIC BIOPOLYMERS AND BIOPARTICLES

FIELD OF THE INVENTION

The present invention relates to the capture of biological species on a support matrix, and more particularly to the selective capture of a desired biopolymer or bioparticle, especially a pathogen, on such a support matrix.

BACKGROUND OF THE INVENTION

Microbial infection in humans and animals is caused by pathogenic microorganisms including, for instance, bacteria, virus, fungi and protozoa. Treatment of bacteria and virus is today primarily effected by antibiotics and antivirals, respectively, which all are low-molecular weight compounds. Antibiotics (such as penicillin and rifampicin) are designed to attack the synthesis of the cell wall and to enter the bacterium and inhibit, for instance, the nucleotide synthesis, DNA replication and protein synthesis, or other important processes, without or only slightly affecting these or other activities in the human cell.

A serious problem is that many bacterial strains have evolved ways to adapt or to become resistant to the currently available antibiotics. The costs of developing new antibiotics is therefore very high and has to a great extent deterred commercial pharmaceutical companies from investing in this area.

Recently, there is a lot of commercial interest and effort in developing so-called cationic peptides. It has been found that virtually all organisms from microbes to man have a variety of cationic peptides that have a potent broad spectrum of antimicrobial activity, including activity against bacteria, eukaryotic parasites, viruses and fungi. The cationic peptides, which typically range in size from 12-50 amino acids and have molecular masses less than 10000, are amphiphatic, meaning that they possess both a hydrophobic group that interacts with, for instance, lipids and a positively charged group that interacts with negatively charged groups in the pathogenic bacterium. These peptides are small enough to penetrate the bacterial wall and affect chemical reactions vital for the metabolism of this bacterium. The action mode is, thus, similar to that of conventional antibiotics and, accordingly, one may expect the resistance problem to be the same.

In addition to the expected resistance problems, cationic peptides are toxic and, further, they cannot be mass-produced in bacteria or fungi in the way many other conventional antimicrobial drugs are produced. Many research groups all over the world in academia and industry have been heavily engaged in this area but no commercial products have been launched in spite of the huge investments.

The difficulties to find novel antibacterials without resistance problems have been compared with the difficulties to "find a needle in a haystack", and there is therefore a need of a completely novel type of antiinfectional.

WO 2009/017456 A1 discloses the development of a different type of antibiotics which does not enter the bacterium (to affect its metabolism) but reacts with the bacterium membrane to immobilize the bacterium and in that way prevents the bacterium from multiplying, thereby making it harmless to the human cell.

That approach is based on the finding that bioparticles, such as cells (including bacteria), virus, fungi, spores, etc have several similarities in their surface properties, including a net surface charge that is negative, external hydrophobic groups, for instance lipids, and external hydrophilic groups, for instance carbohydrates. All types of bioparticles would therefore become attached to a support containing hydrophobic and/or positively charged groups and/or aromatic groups, such as phenol groups. Since it was also known that the more pathogenic a microorganism is, the higher is its surface hydrophobicity and the more it differs from the surface hydrophobicity of human cells, a pathogenic microorganism would attach stronger to a hydrophobic polymer or particle than would a human cell, if at all. As disclosed in WO 2009/017456 A1, pathogenic bioparticles may thus be made nonpathogenic by forming complexes with the above appropriate materials.

It is also found that at least some conventional antibiotics modify the surface structure of bacteria to become more negatively charged and less hydrophobic so that they will not or only weakly attach to human body cells, which was not reported in literature earlier. The common explanation is that conventional antibiotics disturb a chemical reaction of importance for the survival of the pathogen so much that it becomes inactive.

Accordingly, in the above-mentioned WO 2009/017456 A1 a pharmaceutical composition is disclosed which comprises a product for adsorption purposes, preferably in particulate form or polymeric form, especially for oral use or intravenous use, consisting of a support matrix which is insoluble or swelling in water and which supports a hydrophobic entity alone or in combination with a positively charged entity. The support matrix may be a polysaccharide, preferably cellulose. The hydrophobic entity may e.g. be a saturated or unsaturated hydrocarbon chain, and the positively charged entity may e.g. be an amino or ammonium group. A similar product for non-medical or non-therapeutical absorption purposes, especially for the absorption of airborne and/or liquid borne microbes as well as viruses, and microbial antigens including allergens, is disclosed in WO 2004/110193 A1.

As a substantial advantage of the pharmaceutical composition is mentioned the fact that the same method could be used for the attachment of all kinds of bioparticles, which makes the commercial production of the antibacterials, antivirals etc more cost-effective.

In support of the function of the new antibiotics disclosed in WO 2009/017456 A1, it is referred therein (in the "Examples" part) to Wadström, T., et al., _Scand. J. Infect. Dis._ 13:129-137, 1981, which describes experiments where rabbits were orally infected by enterotoxigenic _E. coli_ bacteria to induce diarrhea. By feeding the rabbits with agarose beads derivatized with palmitoyl groups, the diarrhea ceased. No charged groups were attached to the beads.

In WO 2009/017456 A1 it is also referred to a successful treatment of a virus-infected horse by the administration of silica particles derivatized with hydrophobic groups. No charged groups were attached to the beads.

It would, however, be desirable to have access to antibiotics and other anti-microbials which, in addition to the advantages of the antibiotics described in WO 2009/017456 A1, also have a still higher specificity (selectivity). It is an object of the present invention to provide such antiinfectionals.

SUMMARY OF THE INVENTION

To some extent, the present invention is based on a similar approach to that disclosed in the above-mentioned WO 2009/017456 A1, i.e. preventing the bacterium or virus from multiplying by adsorption to a support matrix. However, according to the present invention, it has, surprisingly, been found that the specificity (selectivity) of the support matrix will be still higher if the positive surface charge is exchanged for a negative (or possibly neutral) charge. In contrast to WO 2009/017456 A1, the present invention therefore uses a negative surface charge causing repulsion (rather than attraction by a positive charge) whereby a high selectivity may be created. This is very surprising, the creation of selectivity by introducing the parameter repulsion being—at a first glance—a paradox.

More specifically, the present invention is based on the idea that (i) in living systems, with a few exceptions which refer to toxic substances, the initial net interaction between two biopolymers or bioparticles, or between a biopolymer and a bioparticle, is the net result of the combination of two types of interactions, viz. interactions (repulsions) of electrostatic origin and interactions of hydrophobic origin, and (ii) that any biopolymer or bioparticle can be characterized by the combination of only two parameters, viz. a negative (never positive) net surface charge and a net surface hydrophobicity. Accordingly, any biopolymer or bioparticle will interact with another biopolymer or bioparticle as soon as the hydrophobic net interaction is greater than the electrostatic net repulsion. Further, by proper adjustment of these two parameters, i.e. of the degree of the net interaction with the desired biopolymer or bioparticle, an extremely high selectivity may be created, i.e. no interaction, or only an extremely weak, non-disturbing interaction with human cells can be expected; see Stellan Hjertén: New, General Theory of Interactions in Artificial, as well as Living Systems; Reflections by a Separation Scientist/Biochemist (to be published).

Therefore, according to the invention, the interaction of, for example, a pathogenic particle with a human cell may be at least substantially selectively prevented by capturing the pathogenic bioparticle onto a support matrix modified to have a net hydrophobicity, which is, preferably, somewhat higher than that of the pathogenic bioparticle and with, preferably, the same or a slightly higher negative net surface charge.

A unique feature of the invention is, thus, that interactions between single groups—as in all types of the current antibiotics—are not of interest, but of interest are only net hydrophobic interactions and repulsive net electrostatic interactions, which is an extremely surprising conclusion. Expressed differently, the net interaction between a pathogen and an antiinfectional according to the invention may be adjusted to an optimum value by keeping the hydrophobic interaction constant and slightly modifying the electrostatic repulsion (S. Hjertén, supra). Surprising is also that it is not necessary to select a special type of hydrophobic or negatively charged groups, which is the case for chemical reactions (which all other antibiotics are based on), but not when chemical reactions are exchanged for physical-chemical interactions as the present invention is based on. This is a very important finding which might explain why no class of antiinfectionals of the type described herein has been discussed earlier. The choice of the chemical nature of the charged and hydrophobic groups in the ligands attached to the matrix is thus not critical.

An antiinfectional according to the present invention differs also from the above cationic peptides in that the antiinfectional is negatively charged, possibly non-charged, but never positively charged in terms of net interactions.

Conventional antibiotics, as well as the variant cationic peptides, are so-called biosimilars, i.e. they have a chemical structure similar to substances found in living systems. Therefore the difficulty to find an efficient, highly selective antiinfectional of this type without negative side-effects, including resistance, is obvious and well-known. As is readily seen, with the freedom to choose both material and size of the matrix, the artificial antiinfectionals according to the present invention do not have these disadvantages. Accordingly, one can concentrate all efforts on the selection of the parameters net negative surface charge and net surface hydrophobicity, the selection being relatively simple since these two parameters can experimentally be determined by free zone electrophoresis and hydrophobic-interaction chromatography.

For "free zone electrophoresis", it may be referred to, for instance, Hjertén, S. Free Zone Electrophoresis. *Chromatogr. Rev.* 1967, 9, 122-219; Hjertén, S. Capillary Electrophoresis in Rotation-Stabilized Media. Encyclopedia of Analytical Science, Academic Press, London, 1995, pp. 1106-1112; Hjertén, S. Capillary Electrophoretic Separation in Open Coated Tubes with Special Reference to Proteins, in *Methods of Enzymology* (B. L. Karger, W. S. Hancock, Editors), Academic Press, San Diego, Calif., USA, Vol. 270, 1996, pp. 296-319.

For "hydrophobic-interaction chromatography", it may be referred to, for instance, Hjertén, S., et al. Gradient and Isocratic High-Performance Hydrophobic Interaction Chromatography of Proteins on Agarose Columns. *Journal of Chromatography* 1986, 359, 99-109; and Yao, K. and Hjertén, S. Gradient and Isocratic High-Performance Liquid-Chromatography of Proteins on a New Agarose-Based Anion-Exchanger. *Journal of Chromatography* 1987, 385, 87-98.

The invention is, however, not limited to interaction with pathogens but has wider applicability as will be described below.

Thus, in a broad aspect of the present invention, there is provided a method of preparing a capturing agent for any desired biopolymer or bioparticle, which comprises the steps of:

(i) selecting a desired biopolymer or bioparticle, and
(ii) providing a support matrix modified to have, at predetermined conditions, such a net negative surface charge and net surface hydrophobicity in relation to the net negative surface charge and net surface hydrophobicity of the selected biopolymer or bioparticle that the support matrix is capable of a (highly) selective interaction with and capture of the biopolymer or bioparticle through a resulting net interaction being the net hydrophobic interaction minus the net electrostatic repulsion.

The term "support matrix" as used herein basically refers to a synthetic or natural matrix material which may be used as starting matrix to be modified according to the method above, for instance with hydrophobic and negatively charged ligands.

It is to be noted that, as apparent from the above, the modified support matrix may contain positively charged groups in addition to the negatively charged groups or areas as long as the net surface charge is negative (or at least for some applications possibly neutral).

The modified support matrix may also contain groups or areas capable of specific interaction with the selected biopolymer or bioparticle, for instance phenol groups, borate groups, the polysaccharide-binding groups in lectins, lipopolysaccharides, metal oxides.

Generally, the net negative surface charge of the modified support matrix is in the range of from about 20% lower to about 20% higher than that of the selected biopolymer or bioparticle, and the net surface hydrophobicity is in the range of from about 20% lower to about 20% higher than that of the selected biopolymer or bioparticle. Preferably, the net surface hydrophobicity of the modified support matrix is slightly higher than that of the target biopolymer or bioparticle, and the net negative surface charge is the same or only slightly higher.

The terms "biopolymer" and "bioparticle" as used herein refer to polymers and particles synthesized in living systems. Such polymers include, e.g., proteins, whereas bioparticles include, e.g., pathogens (including viruses, bacteria, fungi, protozoa); erythrocytes, leukocytes and other bioparticles in blood; prostasomes, spermatozoa, cancer cells.

It may be noted that the surface of a virus or bacterium, for example, has the same chemical character as that of proteins and peptides with regard to negative net surface charge and net surface hydrophobicity.

In case the biopolymer or bioparticle has a biological activity, the predetermined conditions include pH and ionic strength values substantially corresponding to those of the (micro) milieu where the biopolymer or bioparticle exhibits its biological activity, typically about pH 7, for instance in blood (although there are many exceptions).

In one embodiment, the preparation of the modified support matrix, typically with hydrophobic and negatively charged groups, or ligands, comprises a screening procedure, wherein support matrices with these ligands are screened for selective interaction with the selected pathogenic biopolymer or bioparticle by varying at least one of the parameters net surface charge and net surface hydrophobicity of the support matrices with their ligands.

In a more specific variant, this may be accomplished by testing non-charged support matrices having a successively increased density of hydrophobic ligands for their capability of capturing the pathogen, and selecting a matrix having such a ligand density that the pathogen only weakly binds to the matrix. A low negative charge is then introduced onto the hydrophobic matrix so that fewer pathogens bind thereto. Finally, the matrix may be provided with additional hydrophobic ligands to slightly increase the hydrophobicity.

In another embodiment, the preparation of the support matrix with ligands comprises a step of measuring at least one of the parameters net surface charge and net surface hydrophobicity of the selected biopolymer or bioparticle, and then modifying the charge and the hydrophobicity of the ligands of the support matrix based on the measured parameter value(s).

In another aspect of the present invention, there is provided a therapeutically active substance, comprising a support matrix designed with ligands to have, at predetermined conditions, such a net negative surface charge and net surface hydrophobicity in relation to the net negative surface charge and net surface hydrophobicity of a selected biopolymer of bioparticle that the support matrix with ligands is capable of a (highly) selective interaction with and capture of the biopolymer or bioparticle through the net interaction created by the net hydrophobic interaction minus the net electrostatic repulsion.

In an additional aspect of the present invention, there is provided a chromatographic bed, comprising a support matrix designed with ligands to have, at predetermined conditions, such a net negative surface charge and net surface hydrophobicity in relation to the net negative surface charge and net surface hydrophobicity of a selected biopolymer of bioparticle that the support matrix with ligands is capable of a (highly) selective interaction with and capture of the biopolymer or bioparticle through the net interaction created by the net hydrophobic interaction minus the net electrostatic repulsion.

In another related aspect of the present invention, there is provided a method for (highly efficient) purification of a (bio)polymer or a (bio)particle which comprises anionic exchange chromatography combined with subsequent hydrophobic-interaction chromatography (both of per se conventional type). Thereby, the above-mentioned characteristic, selectivity-creating parameters negative net surface charge and net surface hydrophobicity are combined in an additional, analogous way to create selectivity. Optionally, the anion-exchanger may be replaced by a cation exchanger, provided that the buffer pH is not low enough to denature the (bio)polymer or (bio)particle. Alternatively, the anion- and cation-exchange steps may be replaced by an electrophoresis step.

In one, presently preferred, embodiment of the above therapeutically active substance aspect of the invention, the therapeutically active substance is an antiinfectional, particularly an antibacterial, antiviral or antimalarian agent, or an anticancer agent.

In still another aspect of the present invention, there is provided a pharmaceutical composition, comprising a therapeutically active substance as defined above, particularly an antiinfectional, such as an antibiotic, or an antiviral, or an anticancer agent.

In yet another aspect of the present invention, there is provided an antiinfectional composition, comprising a support matrix designed to have, at predetermined conditions, such a net negative surface charge and net surface hydrophobicity in relation to the net negative surface charge and net surface hydrophobicity of a selected microorganism that the support matrix is capable of a highly selective interaction with and capture of the microorganism through the net interaction created by the net hydrophobic interaction minus the net electrostatic repulsion.

In another aspect of the present invention, there is provided an assay composition, especially a diagnostic composition, for instance a biomarker composition, comprising a support matrix designed with ligands to have, at predetermined conditions, such a net negative surface charge and net surface hydrophobicity in relation to the net negative surface charge and net surface hydrophobicity of a selected biopolymer or bioparticle, especially a pathogen, that the support matrix is capable of highly selective interaction with the biopolymer or bioparticle, through the net interaction created by the net hydrophobic interaction minus the net electrostatic repulsion.

In still another aspect of the present invention, there is provided a method of treating a subject, especially a human being, which comprises administering to the subject a therapeutically active substance, especially an antiinfectional agent, as defined above, especially orally or nasally or by a parenteral route, or by other procedures.

In another aspect of the present invention, there is provided a method of treating a subject, especially a human being, which comprises extracorporeal treatment of the subject's blood with a capturing agent obtainable by the method defined above for preparing a capturing agent.

In still another aspect of the present invention, there is provided a therapeutically active substance combination, comprising
(i) at least one first component comprising a support matrix designed with ligands to have, at predetermined conditions, such a net negative surface charge and net surface hydrophobicity in relation to the net negative surface charge and net surface hydrophobicity of a selected biopolymer of bioparticle that the support matrix via its ligands is capable of selective interaction with and capture of the biopolymer of bioparticle through the net interaction created by the net hydrophobic interaction minus the net electrostatic repulsion, and
(ii) at least one second component selected from antibiotics of per se conventional type and cationic peptides, and, optionally
(iii) at least one third component selected from substances which activate the immune system.

The above combination may comprise the components as separate entities but, preferably, the second and third components are incorporated into or enclosed within the first component.

In yet another aspect of the present invention, there is provided the use of a capturing agent obtainable by the method defined above for preparing a capturing agent, wherein the use is selected from:
(i) use in chromatography;
(ii) use for the detection of a desired biopolymer or bioparticle, for example for diagnostic purposes;
(iii) use as an antibacterial agent;
(iv) use as an antiviral agent;
(v) use as an antifungal agent;
(vi) use as an anti-parasitic agent, for example an antimalarial agent;
(vii) use in a wound dressing;
(viii) use in a surgical drape;
(ix) use for purification of a liquid or air (especially in filters of various kinds), and
(x) other uses, including use in curtains, car liners, paints, etc.

Preferred embodiments of the different aspects of the invention above are set forth in the dependent claims.

Literature on the theory of separation science is vast, but nowhere the term net interaction is used in the discussion of any separation method; see, for instance, the classical book J. Calvin Giddings, Unified separation science, 1991, a Wiley-Interscience Publication, John Wiley & Sons, Inc., New York.

A more complete understanding of the present invention, as well as further features and advantages thereof, will be obtained by reference to the following detailed description.

DETAILED DESCRIPTION OF THE INVENTION

As mentioned above, the present invention is based on a new theory (developed by the present inventor) of the initial, general net interactions in the body fluids of living systems for biopolymers, such as proteins, and bioparticles, for instance viruses and bacteria, but which also has applications in non-living systems, including those of a chromatographic and electrophoretic nature. This theory can be formulated in four simple postulates (a scientific article, Stellan Hjertén: New, General Theory of Interactions in Artificial, as well as Living Systems; Reflections by a Separation Scientist/Biochemist, describing the theory in detail will be submitted for publication shortly):

1) Electrostatic net attractions (but not repulsions) are forbidden in living systems.

All polymers (for instance proteins) and all particles (for instance viruses and bacteria) in a living system, for instance in a body fluid, can be expected to have the same net surface charge, positive or negative; otherwise the very great number of possible electrostatic attractions between them should cause a chaos.

2) The electrostatic net repulsion, i.e. the repulsion between net negative (never net positive) surface charges is larger than the net hydrophobic interaction to avoid (chaotic) interactions.

The net surface charge of a biopolymer or bioparticle at the pH in its natural milieu is almost always negative, sometimes zero but never positive, except for toxins. Thus, a high, negative mobility of a bioparticle—which is equivalent to a high, negative net surface charge—is a characteristic feature of a bioparticle which should not interact with another bioparticle, i.e. of a non-pathogenic bioparticle. On the other hand, a low, negative mobility of a bioparticle—which is equivalent to a low, negative net surface charge—is a characteristic feature of a bioparticle which should interact with another bioparticle (this is true for both pathogenic and non-pathogenic bioparticles).

3). The hydrophobic interaction is larger than the electrostatic net repulsion to create net interactions.

In this case, the net interaction may create selectivity, which pathogenic bacteria may "take advantage of" in their attachment to the human target cell. It is to be noted that hydrophobic interactions alone cannot create selective bonds. Thus, a high surface hydrophobicity of a bioparticle is an indication that this bioparticle (which may be pathogenic or non-pathogenic) will interact with another bioparticle, particularly if this bioparticle has a low net negative surface charge. On the other hand, a low surface hydrophobicity of a bioparticle is an indication that this bioparticle will not interact with another bioparticle, particularly if this bioparticle has a high net surface charge.

4). In the exceptional case of the electrostatic repulsion=the hydrophobic interaction=zero, other types of bonds than those of electrostatic nature and hydrophobic nature are required.

These bonds involve, for instance, van der Waals and hydrogen bonds as well as induced dipole-dipole interactions and create part of the selectivity between the antigen and protein antibodies raised in experimental animals; shape homology being the other parameter. The selectivity of artificial gel antibodies, which also can be used to interact with and, thus, inactivate antigenic bioparticles, is based on these bonds and shape homology.

The expression "artificial gel antibodies" embraces any antibodies which are built up according to the method as set out in U.S. Pat. No. 5,814,223 for chromatographic media. These antibodies are synthesized by a molecular imprinting approach in such a way that cavities form in the gel, the shape of which is complementary to the shape of the harmful bioparticle, or "antigen", which must be present during the synthesis of the gel antibodies. As mentioned above, this selectivity is strengthened by specific bonds, often hydrogen bonds and induced dipole-dipole interaction, between the antigen and the cavities in the gel antibody. Such artificial antibodies (which are gel antibodies), and the manufacture thereof, are also described in Ivett Basckay et al., *Electrophoresis* 2006, 27, 4682-4687 (gel antibodies against bacteria), Anikó Takátsy et al., J. Sep. Sci. 2006, 29, 2802-2809 (gel antibodies against proteins) and Anikó Takátsy et al., *Electrophoresis* 2007, 28, 2345-2350 (gel antibodies against proteins). The artificial antibodies are gel particles with a size of 0.1 to 0.2 mm (i.e. they are not proteins), and should in general be used as they are without binding to any matrix, such as cellulose or agarose. They are probably more selective than are the conventional protein antibodies, and can be synthesized to interact selectively with both proteins, viruses and bacteria.

Other types of interactions for polymers and particles than the above may occur in biosystems, but they cannot be expected to be predominant, but contribute to the selectivity.

From postulates 1, 2 and 3 above it follows that any biopolymer and bioparticle can be characterized by a combination of only two parameters: a negative, never positive, net surface charge and a net surface hydrophobicity. Accordingly, any bioparticle will interact with another bioparticle as soon as the hydrophobic net interaction is larger than the electrostatic net repulsion (according to postulate 1 electrostatic attractions do not appear in biosystems), and they will not interact if the electrostatic net repulsion is larger than the hydrophobic net interaction. A prerequisite for any bioparticle to be pathogenic to human beings is therefore that it has such surface properties that it does interact with the human target cell and thereby disturbs at least one of its many vital activities.

It is to be noted that the theory above is not applicable to interactions where small (low molecular weight) molecules are involved, because the electrostatic and hydrophobic interactions are too few for selectivity to be created. In this case selectivity is created by chemical reactions on which conventional antibiotics and the cationic peptides are based.

According to the present invention, and based on the above discussion, this interaction between a pathogenic bioparticle and a human target cell may artificially be prevented by capturing the pathogenic bioparticle onto a support matrix modified to have a net hydrophobicity which is, preferably, somewhat higher than that of the pathogen and to have substantially the same or, preferably, a slightly higher, negative net surface charge. The relatively weak initial interaction obtained thereby is of advantage, since the stronger the initial net interaction, the lower is the selectivity of the interaction. This weak initial interaction is reinforced continuously by other interactions occurring later.

The risk that human cells would interact with such a matrix is minimal (and the side effects are thus small) because, as mentioned above, these cells have a high electrophoretic mobility, i.e. a high repulsive negative net surface charge, in order to avoid contacts with other bioparticles, whereas all pathogens seem to have a low negative net surface charge and a high surface hydrophobicity to be able to interact with human cells, which is the prerequisite for them to attack and inactivate these cells.

The strength of these two interactions is pH dependent. At low pH the electrostatic repulsion between bioparticles is weaker, whereas the hydrophobic interaction is stronger, which makes it possible to fine-adjust or tailor-make the net interaction and thus create extremely high selective interactions.

An antiinfectional, such as an antibiotic, which should be highly selective for any desired pathogen may, thus, be prepared by proper design of a matrix as described above. Such an antiinfectional would clearly meet the requirements a) and b), and most likely also c), of the following requirements for an ideal alternative to conventional antibiotics:

a) The mechanism of the method for inactivation of the pathogen should be known in detail, simple, applicable to all types of pathogenic particles and such that there is no or only a small risk of resistance; if resistance occurs, it should be easy to modify the synthesis of the antiinfectional.

b) The method for the synthesis of the antiinfectional should be straight-forward, cost-effective and flexible which is extremely important in case of bacterial resistance.

c) The antiinfectional should have a surface structure such that, in practice, it can be expected to have no or only negligible side-effects.

In chromatographic terms, the antiinfectional may be defined as beads used in hydrophobic-interaction chromatography (HIC) with ligands of such a hydrophobicity, density and net negative surface charge that the pathogen is moderately adsorbed, but the human target cell not at all, or possibly only slightly.

For successful treatment of, for instance, a bacterial or viral infection, the ligands in the antiinfectional matrix should interact with the bacterial membrane or the virus capside (to prevent the bioparticles from multiplying), but not or only slightly interact with the membrane of any human or animal cell in order not to disturb its normal activities. An experimental, correct adjustment of these two key parameters (net surface hydrophobicity and net negative surface charge) is therefore essential in order to achieve a highly selective capture of the pathogen without negative side effects.

It is readily seen that a support matrix modified as described above with regard to the two key parameters net surface hydrophobicity and net negative surface charge to be capable of capturing a selected biopolymer or biomolecule, may have other uses than as an antiinfectional, e.g. in chromatography, as a reagent in assays for the selective capture of a biomarker (a protein, a virus, a bacterium, etc), and of bacteria in a wound, as will be described further on.

The support matrix and its substitution with charged and hydrophobic groups or ligands, respectively, will now be described in more detail.

Selection of the Amphiphilic Support Matrix

The expression "support matrix" as used herein embraces, in a broad sense, any matrix which is built up of a material which is aqueous-insoluble and/or aqueous-soluble and/or aqueous-swelling, and large enough not to enter cell membranes.

The support matrix is suitably an inert, non-charged, (preferably strongly) hydrophilic matrix as is used as beds, also called stationary phases or supporting media, in electrophoretic and chromatographic methods. Preferably, the matrices have hydroxyl groups as reaction centres for simple covalent attachment of both hydrophobic and negatively charged ligands, and, when required, the support matrix should also be biocompatible. The hydrophilicity of the supporting matrix itself ensures that non-selective adsorption is avoided, and that only the ligands, not the matrix itself, interact with the pathogen, or more generally, the biopolymer or bioparticle.

A support matrix with the above properties has the following advantages for the design of an antiinfectional: a) a high selectivity for the capture of the pathogen of interest, since interactions other than those originating from the hydrophobic and negative nature of the ligand will be strongly suppressed or eliminated; and b) the presence of and the access to many hydroxyl groups gives flexibility in the selection of methods for the attachment of the hydrophobic and negatively charged ligands and decreases the risk of secondary, selectivity-decreasing hydrophobic interactions.

Exemplary support matrices having a high biocompatibility include matrices of agarose and dextran, and also of cellulose (if the carboxylic groups are negligible), e.g. cross-linked cellulose. Agarose beads may be considered as a more or less ideal matrix for the coupling of the hydrophobic and negative ligands when synthesizing a capturing agent according to the present invention, such as an antiinfectional, although in special cases other matrices may be preferable. An advantage of the above matrices is that the coupling chemistry for coupling desired ligands to the matrix is well known, for instance from the field of chromatography.

Other exemplary support matrix materials include silica beads coated with a hydrophilic polymer, polyacrylamide and polyvinylalcohol (both are hydrophilic and non-charged). Still other examples include polygalactanes (comprising polygalactose units), starch and guar gum, provided that these biopolymers are non-charged, or possibly weakly negatively charged.

The support matrix may be in the form of (gel) particles or a polymer. In the latter case, the molecular weight of the polymer should, at least when used as an antiinfectional or for other therapeutic purposes, be so high that it cannot penetrate the wall of the human target cell and disturb its metabolic processes or other activities.

An alternative support matrix is based on a bioparticle or a protein naturally present in a body fluid, especially an immunoglobulin (which has a very low surface hydrophobicity and a net surface charge close to zero) or a polymer of an immunoglobulin.

Another alternative support matrix is a mixture of one of the above support matrices and vegetable extracts known to affect the immune system, such as alginates, laminarins, fucoidans, polyphenols, etc.

Each synthesis of an antiinfectional requires a thorough selection of both matrix and ligand. Thus, for instance, an antiinfectional for treatment of infections in the abdomen could be composed of purified cellulose with alkyl ligands, since both these components are part of our daily food and therefore likely to be accepted, also when combined. Such an antiinfectional would probably not, or only slightly, affect negatively the metabolism or other reactions in the intestine.

An appropriate hydrophilic matrix for an antiinfectional may be of a size similar to that of the pathogen or larger, although nanoparticles of, for instance, cross-linked dextran might also be contemplated.

Administration of an antiinfectional according to the invention may, for example, be effected orally or nasally or by a parenteral route. Due to their relatively small size and a negative net surface charge close to zero at pH around 7, immunoglobulins, or polymers thereof, could serve as matrices for an antiinfectional when used for injection into blood, as could also nanoparticles. Such antiinfectionals could also be used in the form of a spray, especially for treatment of the upper respiratory tract or for injection through the skin.

Selection of the Net Negative Surface Charge of the Matrix with its Ligands

This parameter should have a value close to, and preferably a slightly more negative value than that of the biopolymer or bioparticle, e.g. a pathogen. A desired negative charge may be obtained by coupling negatively charged ligands to the matrix. Such ligands may in turn be prepared by covalent coupling of negative groups, such as carboxyl groups, to a hydrophilic non-charged ligand with, preferably, a chain length similar to that of the hydrophobic ligand (described below).

To modify the basic support matrix with negatively charged ligands, one may proceed as follows. First, the mobility of the biopolymer or bioparticle, especially a pathogen, is determined by free zone electrophoresis (FZE) in a revolving tube (the mobility is proportional to the net surface charge, Ze). Hydrophilic, negatively charged ligands are then coupled to the hydrophilic support matrix, the ligand density being successively increased until a sample of the matrix migrates with the mobility of the pathogen or slightly faster. Hydrophobic groups or ligands are then attached as described below. An alternative procedure not requiring FZE will be described further below.

To incorporate negative groups into the matrix, for instance, the same methods as used for the synthesis of a cation exchanger may be used. Such negative groups, e.g. carboxyl groups, are preferably covalently linked to a hydrophilic ligand which suitably has a length similar to that of the hydrophobic ligand.

Selection of the Net Surface Hydrophobicity

The optimum hydrophobicity of the modified support matrix is where the biopolymer or bioparticle of interest, such as a pathogen, starts to be moderately adsorbed. This may be determined by using the same ligand in a series of experiments, where the ligand density is increased step-wisely in order to find the optimum hydrophobicity, i.e. the ligand density at which the pathogen starts being adsorbed. A matrix with this ligand density, or somewhat higher, may then be used as at least a prototype for an antiinfectional, for example.

An alternative, although a more complicated one, is to choose a constant ligand density and vary (typically increase) continuously the hydrophobicity of the ligand, e.g. different chain lengths.

Typically, hydrocarbon chains may be used as hydrophic ligands. Appropriate methods for coupling of such hydrophobic ligands to the support matrix include those conventionally used for coupling of hydrophobic constituents to hydrophobic-interaction chromatography (HIC) media. The hydrocarbon chains may be saturated or unsaturated with a chain length of, generally, from C5 to C25, typically an alkyl or alkylene chain, preferably with a chain length of from C8 to C18, more preferably a saturated or unsaturated hydrocarbon chain with a chain length of from C12 to C18.

As alternatives to hydrophobic alkyl or alkylene ligands may be mentioned non-toxic lipopolysaccharides and hydrophobic aromatic compounds. Mixtures of different ligands may, of course, also be used. Polysaccharides interact with phenol groups on a bioparticle (for instance a bacterium) surface. Lipid groups create hydrophobic interaction.

Optionally, non-hydrophobic ligands may be used in combination with hydrophobic ligands to adjust the net interaction of the modified support matrix with a pathogenic bioparticle. Such non-hydrophobic ligands include (negatively charged) borate or boronate groups which are also known to interact with carbohydrates, specifically those having two hydroxyl groups in cis-position. Since carbohydrates are surface components of many bioparticles, including pathogens, an antiinfectional with borate or boronate groups should, therefore, bind to the surface of a pathogen. Other carbohydrate binding groups include aromatic compounds, such as phenols (see above). For instance, polyphenol groups may therefore, optionally, be combined with the hydrophobic ligands. The sugar-binding domain of lectins is another alternative ligand.

While the above-described determination of optimal values of the parameters negative net surface charge and net surface hydrophobicity for selective capture of a pathogen makes use of free zone electrophoresis (FZE), these parameters may be determined by an alternative technique which is easy to apply and may be performed in any life science laboratory.

A preferred matrix material for this purpose has the property to be strongly hydrophilic by groups containing many hydroxy groups and accessible for the attachment of hydrophobic ligands. An exemplary commercial product having this property is Sepharose® (GE Healthcare, Uppsala, Sweden), and chemical methods for the attachment of different ligands, including alkyl groups, are well known to a person skilled in the art.

To carry out the determination, a series of Sepharose® beads with successively increasing densities of a hydrophobic ligand is synthesized. A bead useful as an antiinfectional, e.g for capturing a pathogenic bacterium, should have such a ligand density that the pathogenic bacteria are only weakly attached. This optimal density can easily be experimentally established by a determination of the number of the bacteria in the presence of sedimented Sepharose® beads with somewhat different ligand densities and non-derivatized beads as a blank (techniques for such bacterial count are well known). While such neutral, hydrophobic Sepharose® beads may be used as candidates for an antiinfectional according to the invention, a higher selectivity would be obtained by introducing negatively charged ligands onto the bead to obtain a low negative net surface charge, and then, if necessary, increasing somewhat the hydrophobicity by coupling additional hydrophobic ligands to increase their density on the bead.

Expressed differently, the hydrophobocity of the Sepharose® bead is successively increased by increasing the density of hydrophobic ligands until the pathogen weakly (or barely) binds to the bead. A weak negative charge is then introduced so that the pathogen binds somewhat less, and additional hydrophobic ligands are then, optionally, coupled to the bead until the pathogen again weakly (or barely) binds to the bead.

The composition, the ionic strength and the pH of the medium in which the matrix is suspended in the tests should, of course, in the case of e.g. an antiinfectional, be adapted to the medical and pharmaceutical requirements and the physiological (micro) milieu where the antiinfectional is assumed to be active. While the pH value of this micro-milieu is often about 7, the interaction pH for an antiinfectional for diseases caused by, for instance, satellite tobacco necrosis virus (STNV) and by *Helicobacter pylori* is far below pH 7.

In an antiinfectional which is to be active at a relatively low pH, such as in the stomach (for treatment of gastric ulcer), the charged groups of the negatively charged ligands, such as carboxyl groups, are protonated (i.e. non-charged) and thus will lose their electrostatically repelling effect, resulting in a stronger over-all net interaction between the antiinfectional and the pathogen, but also in a weaker repulsion to the human cells in solutions and tissues at higher pH. In these antiinfectionals, the pK value of the negative group should therefore have such a value that its net surface charge is high at a pH above that in the stomach but lower and close to the optimum value for interaction with *Helicobacter pylori* in the stomach in order to get a high selectivity with minimum side effects.

On the other hand, when the antiinfectional is to be active at a relatively high pH, ligands which are weak bases (amines) and weak acids (carboxyl groups) may be selected for the selective capture of the pathogen. At high pH the amine groups are non-charged whereas the carboxyl groups are charged. Therefore, the electrostatic repulsion between such an antiinfectional and human cells is larger at this pH (the ligand density being, as always, chosen such that the electrostatic repulsion is slightly lower than the hydrophobic interaction at this pH), i.e. there is an interaction but weaker than that at a lower pH. The side effects of this antiinfectional are thereby lower.

The pathogen will not multiply upon cultivation in the presence of the matrix with ligands attached, since it is immobilized. However, not to disturb (or to minimize) the normal activities of human cells, the net interaction of the matrix with the pathogen should not be higher than necessary to immobilize and thereby inactivate the pathogen. This may, as mentioned above, be achieved by decreasing or increasing (1) the hydrophobicity of the ligand or (2) the ligand density. In the ideal case, the antiinfectional should interact highly selectively with the pathogen, i.e. not at all with human cells.

An antiinfectional as described above may with advantage be used also for diagnosis of diseases caused by pathogens, i.e. as a biomarker.

A pharmaceutical composition comprising a therapeutic agent according to the present invention, such as an antiinfectional, may be in formulations for oral, rectal, parenteral or other modes of administrations. The pharmaceutically acceptable carrier may be in form of a solid, semi-solid or liquid diluent, or capsule. Usually the amount of active agent is between 0.1-95% by weight of the preparation, between 0.2-20% by weight in preparations for parenteral use and between 1-50% by weight in preparations for oral administration.

In the preparation of pharmaceutical formulations in form of dosage units for oral administration the carrier may be a solid, powdered carrier, such as lactose, saccharose, sorbitol, mannitol, starch, amylopectin, cellulose (derivates), agarose, dextran (cross-linked or not), gelatin or another suitable carrier. The mixture is then processed into granules or pressed into tablets. Granules and tablets may be coated with an enteric coating which protects the active compound from acid catalysed degradation as long as the dosage form remains in the stomach. The enteric coating is chosen among relevant pharmaceutically acceptable enteric-coating materials. To the coating various dyes may be added in order to distinguish among tablets or granules with different amounts of the active compound present. The carrier and the enteric coating must not interact with the active substance.

Solutions for parenteral administration may be prepared as solutions of a product prepared according to the method of the invention in pharmaceutically acceptable solvents, preferably at a concentration from 0.1 to 10% by weight. These solutions may also contain stabilizing agents and/or buffering agents and may be manufactured in different unit dose ampoules or vials. Solutions for parenteral administration may also be prepared as dry preparations to be reconstituted with a suitable solvent extemporaneously before use.

As mentioned above, conventional antibiotics suffer from the problem of resistance (as will most likely also the cationic peptides). This is due to their mode of action, i.e. to disturb crucial chemical reactions in a bacterial cell. The bacterium has, however, the property to synthesize another compound with the same property, this being the reason why the bacteria are resistant to conventional antibiotics.

However, in contrast, the interaction between a pathogenic bacterium and a human cell, is of physical-chemical character rather than chemical. Thus, if the bacterium changes its physical-chemical interaction character by mutation in response to treatment with an antiinfectional according to the present invention (the interaction mechanism is also physical-chemical), the bacterium will heavily decrease or lose its capability of interaction with the human cells (meaning suicide).

As briefly mentioned above, it is known that at least some classical antibiotics at sub-inhibitory concentrations have the property to decrease the net surface hydrophobicity and at the same time increase the net negative surface charge of pathogenic bacteria (Tylewska, S. K., Wadström T., and Hjertén, S. The Effect of Subinhibitory Concentrations of Penicillin and Rifampicin on Bacterial Cell Surface Hydrophobicity and on Binding to Pharyngeal Epithelial cells. *Journal of Antimicrobial Chemotherapy* 1980, 6, 292-294, and Smyth, C. J., Jonsson P., Olsson E., Söderlind, O., Rosengren, F., Hjertén S. and Wadström T. Differences in Hydrophobic Surface Characteristics of Porcine Enteropathogenic *Escherichia coli* with and without K 88 Antigen as revealed by Hydrophobic Interaction Chromatography. *Infection and Immunity* 1978, 22, 462), i. e. these bacteria have lost their property to adhere to human cells and thus to disturb their normal activities; from being pathogenic they have turned to being non-pathogenic. However, at this stage they can be expected to attach to any hydrophobic surface in form of biofilms, provided the surface is non-charged, such as a catheter surface of polystyrene, which also is evident from many experiments, referred to in literature. In this state they are dormant and may survive for long periods of time and are, accordingly, difficult to erradicate (Stellan Hjertén: New, General Theory of Interactions in Artificial, as well as Living Systems; Reflections by a Separation Scientist/Biochemist; to be published). Can the present world-wide, serious resistance problem be explained in these terms? If so, one should select antibiotics among those which do not form biofilms, provided such antibiotics do exist. Or do some antibiotics change their surface properties without creating biofilms? Also in this case it is easy to synthesize antiinfectionals with the properties discussed herein. It should be underlined that the design and the synthesis of the antiinfectionals according to the present invention can quickly and easily be modified whatever the reasons are.

The combination of the parameters net surface hydrophobicity and net negative surface charge of the capturing agent of the present invention is of such nature that it with advantage may have numerous uses also outside the bio-world, i.e. in semi- or non-living systems, including, for instance, to purify water, prolong the life time of painted out-door facades, in antiseptic surfaces, in curtains, filters to purify air/liquid from pathogens, including viruses, bacteria, parasites, fungi, moulds, Anthrax, etc in hospitals, cinemas, schools, public halls, and with advantage in wound dressings, etc, just to mention a few.

As mentioned above, the present invention may have chromatographic applications. To this end, a chromatographic bed comprises a support matrix designed as above, i.e. with ligands which at predetermined conditions have such a net negative surface charge and net surface hydrophobicity in relation to the net negative surface charge and net surface hydrophobicity of a selected (bio)polymer of (bio)particle that the chromatographic bed is capable of a highly selective interaction with and capture of the biopolymer or bioparticle. This chromatographic product can be used not only for diagnosis of a disease by selective capture of a biomarker, but also for medical treatment of the disease by capture of the pathogen (a protein, virus, bacterium, cancer cell, etc). Such a chromatographic product is the chromatographic counterpart of "Antiinfectional B", discussed in the aforementioned article by Stellan Hjertén: New, General Theory of Interactions in Artificial, as well as Living Systems, to be published.

In a related chromatographic application, a highly efficient purification of a (bio)polymer or a (bio)particle may be achieved by a conventional anionic exchange chromatography experiment combined with a subsequent conventional hydrophobic-interaction chromatography (HIC) experiment, i.e. the characteristic, selectivity-creating parameters negative net surface charge and net surface hydrophobicity are again combined in an additional, analogous way to create selectivity. These experiments are typically performed in a laboratory or pilot plant, i.e. a non-living system. Therefore, the anion-exchanger may be replaced by a cation exchanger, provided that the pH of the buffer is not so low that the (bio)polymer or the (bio)particle will be denaturated. The anion- and cation-exchange steps in the above experiment may be replaced by an electrophoresis experiment.

Therefore, the following two-step procedure, based on the theory discussed herein, guarantees a high degree of purity of any (bio)polymer and (bio)particle:

Step 1. Purification by anion-exchange chromatography or zone electrophoresis (the separations in this step are based on net negative surface charge). The chromatographic fractions containing the (bio)polymer or (bio)particle are then transferred to a HIC-bed for further purification (step 2 below).

Step 2. Hydrophobic-interaction chromatography.

The invention will be further illustrated by the following non-limiting Examples.

Example 1

Creation of High Selectivity in the Capture/Immobilization of a Pathogen a) The electrophoretic mobility of the pattern is determined by free zone electrophoresis (FZE) in a (buffer) solution of the same chemical composition and pH as that where the pathogen (for instance a virus or a bacterium) is expected to attack the human or animal cell (the same requirement must be fulfilled also in b) below). Observe that the mobility is proportional to the net surface charge of a particle (one of the two parameters of importance in the design of the antiinfectional; net surface hydrophobicity is the other parameter).

Hydrophilic ligands with a negative charge, for instance a pentamer of glucose units with a carboxylic group attached to the free end of the pentamer, are attached to a hydrophilic matrix, for instance agarose beads. The coupling of the glucose pentamer to the agarose beads may conveniently be performed by conventional methods, for example, as described in Hjertén, S., et al. Hydrophobic Interaction Chromatography. The synthesis and the Use of Some Alkyl and Aryl Derivatives of Agarose. *Journal of Chromatography* 1975, 101, 281-288. The ligand density is increased successively until the mobility of the substituted matrix is the same as that of the pathogen. Observe that the mobility—and therefore also the net surface charge—of a bacterium or the agarose beads is roughly independent of the size of the bacterium and that of the beads.

b) Hydrophobic ligands, for instance selected from C5- to C18-alkyl groups, are successively attached to the above negatively charged agarose beads, until the pathogen begins to be attached. For the coupling of the alkyl ligands to the agarose beads, a coupling method is used which does not introduce any charge, e.g. a method as described in Hjertén, S., et al. (1975) above, or in Rosengren, J., et al. Hydrophobic-Interaction Chromatography on Non-Charged Sepharose® Derivatives. Binding of a Model Protein Related to Ionic Strength, Hydrophobicity of the Substituent, and Degree of Substitution (Determined by NMR). *Biochimica et Biophysica Acta* 1975, 51-61. These agarose beads, or beads with somewhat higher ligand density, are then used as an antiinfectional.

The length of the hydrophobic ligands should be about the same as that of the negatively charged ligands.

For instance, to fight *Heliobacter pylori* (the colonizer causing inflammation and gastritis in the mucosa) the pH should be low.

Example 2

Simple, Efficient One-Step Chromatographic Purification of a Polymer (For Instance a Protein) or a Particle (For Instance a Pathogenic Virus or Bacterium)

The procedure is analogous to that described In Example 1 above for the design of an antiinfectional. The beads should have a ligand density so low that the purification can be achieved in the isocratic (not gradient) mode (Hjertén, S., et al., Gradient and Isocratic High-Performance Hydrophobic Interaction Chromatography of proteins on Agarose Columns. *Journal of Chromatography* 1986, 359, 99-109; Yao, K. and Hjertén, S., Gradient and Isocratic High-Performance Hydrophobic Interaction Chromatography of proteins on a New Agarose-Based Anion-Exchanger. *Journal of Chromatography* 1987, 385, 87-98; and Hjertén, S., Thermodynamic Treatment of Partition Experiments with Special Reference to Molecular_sieve Chromatography. *Journal of Chromatography* 1970, 50, 189-208).

No expensive equipment for gradient elution is required, which is particularly important for purification on industrial scale.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A method of preparing a capturing agent for a selected biopolymer or bioparticle, comprising the steps of:
   a) selecting a desired biopolymer or bioparticle, and
   b) providing a support matrix modified to have, at predetermined conditions, such a net negative surface charge and net surface hydrophobicity in relation to the net negative surface charge and the net surface hydrophobicity of the selected biopolymer or bioparticle that the modified support matrix is capable of selective interaction and capture of the biopolymer or bioparticle through a resulting net hydrophobic interaction being the actual hydrophobic interaction minus the actual electrostatic repulsion.

2. The method according to claim 1, wherein at least one of the net surface charge of the modified support matrix and the net surface hydrophobicity of the support matrix is in the range of from about 20% lower to about 20% higher than that of the selected biopolymer or bioparticle.

3. The method according to claim 1, wherein providing the modified support matrix comprises screening support matrices for selective interaction with the selected biopolymer or bioparticle by varying at least one of the parameters net surface charge and net surface hydrophobicity of the support matrices.

4. The method according to claim 3, which comprises keeping the net surface charge constant and varying the net surface hydrophobicity.

5. The method according to claim 3, which comprises keeping the net surface hydrophobicity constant and varying the net surface charge.

6. The method according to claim 3, which comprises varying the net surface hydrophobicity of an at least substantially non-charged support matrix to select a support matrix having a hydrophobicity such that the selected biopolymer or bioparticle weakly binds thereto, adding a low negative net surface charge to the support matrix, and, optionally, adding a small amount of additional hydrophobicity to the support matrix.

7. The method according to claim 1, wherein providing the modified support matrix comprises the step of measuring at least one of the parameters net surface charge and net surface hydrophobicity of the selected biopolymer or bioparticle.

8. The method according to claim 7, wherein the net surface charge is measured by free zone electrophoresis, and the net surface hydrophobicity is measured by hydrophobic-interaction chromatography or by a precipitation technique.

9. The method according to claim 1, further comprising the step of isolating the selected biopolymer or bioparticle from a biological fluid.

10. The method according to claim 9, wherein the step of isolating the selected biopolymer or bioparticle comprises:
    a) purification by anion-exchange chromatography or zone electrophoresis; and
    b) hydrophobic-interaction chromatography.

11. The method according to claim 1, wherein the selected biopolymer is a protein or a polypeptide.

12. The method according to claim 1, wherein the selected biopolymer or bioparticle is a pathogen.

13. The method according to claim 1, wherein the biopolymer or bioparticle has a biological activity, and said predetermined conditions include pH and ionic strength values substantially corresponding to those of the milieu where the biopolymer or bioparticle exhibits its biological activity.

14. The method according to claim 1, wherein the modified support matrix comprises an inert non-charged hydrophilic matrix supporting (i) hydrophilic groups or ligands which are negatively charged at said predetermined conditions, and (ii) hydrophobic groups or ligands.

15. The method according to claim 14, wherein the hydrophilic matrix is mixed with at least one vegetable extract, preferably selected from fucoindans, alginates, laminarins, and polyphenols, which are known to activate the immune system.

16. The method according to claim 14, wherein the hydrophilic support matrix comprises a polymer or a particle selected from agarose, dextran, cellulose, starch, guar gum, polyacrylamide, polyvinylalcohol, and coated silica beads.

17. The method according to claim 1, wherein the modified support matrix comprises a protein or polypeptide.

18. The method according to claim 1, wherein the modified support matrix comprises a bioparticle or a nanoparticle.

19. The method according to claim 14, which comprises the sequential steps of providing the inert non-charged hydrophilic matrix, coupling hydrophilic, negatively charged ligands to the matrix, and coupling hydrophobic ligands to the matrix.

20. The method according to claim 19, wherein the negatively charged ligands and the hydrophobic ligands comprise molecular chains of substantially the same length.

21. The method according to claim 14, wherein the modified support matrix further comprises at least one group or ligand capable of selectively binding to the biopolymer or bioparticle.

22. The method according to claim 21, wherein the selectively binding group or ligand comprises a carbohydrate binding group or a carbohydrate-interacting group in lectins.

23. A therapeutically active substance, comprising a support matrix modified to have, at predetermined conditions, such a net negative surface charge and net surface hydrophobicity in relation to the net negative surface charge and net surface hydrophobicity of a selected biopolymer or bioparticle that the modified support matrix is capable of selective interaction with and capture of the biopolymer of bioparticle through the net interaction created by the net hydrophobic interaction minus the net electrostatic repulsion.

24. The therapeutically active substance according to claim 23, which is selected from an antibiotic; an antiviral agent; an antifungal agent; an anti-malarial agent; and an anticancer agent.

25. A pharmaceutical composition, comprising a therapeutically active substance according to claim 23.

26. An antimicrobial composition, comprising a support matrix modified to have, at predetermined conditions, such a net negative surface charge and net surface hydrophobicity in relation to the net negative surface charge and the net surface hydrophobicity of a selected biopolymer or bioparticle, including microorganisms, that the support matrix is capable of selective interaction with and capture of the biopolymer or bioparticle through the net interaction created by the net hydrophobic interaction minus the net electrostatic repulsion.

27. A method of treating a subject, which comprises administering to the subject a therapeutically active substance according to claim 23.

28. A method of treating a subject, which comprises extracorporeal treatment of the subject's blood with a capturing agent obtainable by the method according to claim 1.

* * * * *